US009463018B2

(12) United States Patent
Milliman

(10) Patent No.: US 9,463,018 B2
(45) Date of Patent: Oct. 11, 2016

(54) ANVIL FOR SURGICAL STAPLER

(71) Applicant: Covidien LP, Mansfield, MA (US)

(72) Inventor: Keith Milliman, Bethel, CT (US)

(73) Assignee: Covidien LP, Mansfield, MA (US)

(*) Notice: Subject to any disclaimer, the term of this patent is extended or adjusted under 35 U.S.C. 154(b) by 658 days.

(21) Appl. No.: 13/897,473

(22) Filed: May 20, 2013

(65) Prior Publication Data

US 2013/0253578 A1    Sep. 26, 2013

Related U.S. Application Data

(62) Division of application No. 12/688,870, filed on Jan. 16, 2010, now Pat. No. 8,453,913.

(60) Provisional application No. 61/150,429, filed on Feb. 6, 2009.

(51) Int. Cl.
A61B 17/068 (2006.01)
A61B 17/115 (2006.01)
A61B 17/072 (2006.01)
A61B 17/00 (2006.01)
A61B 17/29 (2006.01)

(52) U.S. Cl.
CPC ........... *A61B 17/068* (2013.01); *A61B 17/115* (2013.01); *A61B 17/072* (2013.01); *A61B 17/07207* (2013.01); *A61B 17/1155* (2013.01); *A61B 2017/00526* (2013.01); *A61B 2017/00831* (2013.01); *A61B 2017/00853* (2013.01); *A61B 2017/07214* (2013.01); *A61B 2017/07257* (2013.01); *A61B 2017/07264* (2013.01); *A61B 2017/2927* (2013.01); *Y10T 29/49908* (2015.01)

(58) Field of Classification Search
CPC ............. A61B 17/068; A61B 17/072; A61B 17/07207; A61B 17/07292; A61B 17/115; A61B 17/1155; A61B 2017/07214; A61B 2017/07257; A61B 2017/07285
USPC .......... 227/19, 175.1, 176.1, 180.1; 606/213, 606/219, 137, 143, 151, 153
See application file for complete search history.

(56) References Cited

U.S. PATENT DOCUMENTS

| 2,073,960 A | 3/1937 | S.A. Crosby |
| 3,193,165 A | 7/1965 | Akhalaya et al. |
| 3,388,847 A | 6/1968 | Kasulin et al. |

(Continued)

FOREIGN PATENT DOCUMENTS

| EP | 0552423 | 7/1993 |
| EP | 1647230 | 4/2006 |

(Continued)

OTHER PUBLICATIONS

Canadian Office Action dated Nov. 16, 2015, issued in Canadian Application No. 2,691,181.

(Continued)

*Primary Examiner* — Scott A. Smith

(57) ABSTRACT

An anvil assembly for use therewith a surgical fastener applying apparatus including an anvil plate and an anvil head configured and dimensioned to support the anvil plate. The anvil plate and the anvil head may be formed from different materials. The anvil plate can include a tapered outer side wall allowing the anvil assembly to realize a substantially uniform proximal-most surface upon assembly.

10 Claims, 12 Drawing Sheets

(56) References Cited

U.S. PATENT DOCUMENTS

| | | |
|---|---|---|
| 3,499,591 A | 3/1970 | Green |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,319,576 A | 3/1982 | Rothfuss |
| 4,350,160 A | 9/1982 | Kolesov et al. |
| 4,476,863 A | 10/1984 | Kanshin et al. |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,632,290 A | 12/1986 | Green et al. |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,754,909 A | 7/1988 | Barker et al. |
| 4,767,044 A | 8/1988 | Green |
| 4,817,847 A | 4/1989 | Redtenbacher et al. |
| 4,873,997 A | 10/1989 | Marshall |
| 4,903,697 A | 2/1990 | Resnick et al. |
| 4,907,591 A | 3/1990 | Vasconcellos et al. |
| 4,957,499 A | 9/1990 | Lipatov et al. |
| 4,962,877 A | 10/1990 | Hervas |
| 5,032,354 A | 7/1991 | Nakanishi et al. |
| 5,042,707 A | 8/1991 | Taheri |
| 5,047,039 A | 9/1991 | Avant et al. |
| 5,104,025 A | 4/1992 | Main et al. |
| 5,139,513 A | 8/1992 | Segato |
| 5,188,638 A | 2/1993 | Tzakis |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant |
| 5,314,436 A | 5/1994 | Wilk |
| 5,330,486 A | 7/1994 | Wilk |
| 5,333,773 A | 8/1994 | Main et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,439,156 A | 8/1995 | Grant et al. |
| 5,445,644 A | 8/1995 | Pietrafitta et al. |
| 5,464,415 A | 11/1995 | Chen |
| 5,480,089 A | 1/1996 | Blewett |
| 5,505,363 A | 4/1996 | Green et al. |
| 5,533,661 A | 7/1996 | Main et al. |
| 5,588,579 A | 12/1996 | Schnut et al. |
| 5,608,576 A | 3/1997 | Han et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,709,335 A | 1/1998 | Heck |
| 5,715,987 A | 2/1998 | Kelley et al. |
| 5,720,755 A | 2/1998 | Dakov |
| 5,732,872 A | 3/1998 | Bolduc et al. |
| 5,749,896 A | 5/1998 | Cook |
| 5,814,055 A | 9/1998 | Knodel |
| 5,839,639 A | 11/1998 | Sauer et al. |
| 5,855,312 A | 1/1999 | Toledano |
| 5,868,760 A | 2/1999 | McGuckin et al. |
| 5,881,943 A | 3/1999 | Heck et al. |
| 5,911,352 A | 6/1999 | Racenet et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,209,773 B1 | 4/2001 | Bolduc et al. |
| 6,241,140 B1 | 6/2001 | Adams et al. |
| 6,244,491 B1 | 6/2001 | Kandasamy et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,402,780 B2 | 6/2002 | Williamson, IV et al. |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,681,979 B2 | 1/2004 | Whitman |
| 6,685,079 B2 | 2/2004 | Sharma et al. |
| 6,695,198 B2 | 2/2004 | Adams et al. |

(56) References Cited

U.S. PATENT DOCUMENTS

| | | |
|---|---|---|
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,846,769 B2 | 1/2005 | Nicolo |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,953,138 B1 | 10/2005 | Dworak et al. |
| 6,978,922 B2 | 12/2005 | Bilotti et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,182,239 B1 | 2/2007 | Myers |
| 7,207,168 B2 | 4/2007 | Deopker et al. |
| 7,207,471 B2 | 4/2007 | Heinrich et al. |
| 7,220,237 B2 | 5/2007 | Gannoe et al. |
| 7,235,089 B1 | 6/2007 | McGuckin, Jr. |
| RE39,841 E | 9/2007 | Bilotti et al. |
| 7,300,444 B1 | 11/2007 | Nielsen et al. |
| 7,303,106 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,398,907 B2 | 7/2008 | Racenet et al. |
| 7,401,722 B2 | 7/2008 | Hur |
| 7,410,086 B2 | 8/2008 | Ortiz et al. |
| 7,422,138 B2 | 9/2008 | Bilotti et al. |
| 7,455,676 B2 | 11/2008 | Holsten et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,546,939 B2 | 6/2009 | Adams et al. |
| 7,546,940 B2 | 6/2009 | Milliman et al. |
| 7,585,306 B2 | 9/2009 | Abbott et al. |
| 7,585,307 B2 | 9/2009 | Fontayne et al. |
| 7,758,613 B2 | 7/2010 | Whitman |
| 7,882,995 B2 | 2/2011 | McAlister et al. |
| 7,942,302 B2 | 5/2011 | Roby et al. |
| 7,951,166 B2 | 5/2011 | Orban et al. |
| 7,980,443 B2 | 7/2011 | Scheib et al. |
| 8,006,701 B2 | 8/2011 | Bilotti et al. |
| 8,025,199 B2 | 9/2011 | Whitman et al. |
| 8,128,645 B2 | 3/2012 | Sonnenschein et al. |
| 8,142,449 B2 | 3/2012 | Kohl et al. |
| 8,181,840 B2 | 5/2012 | Milliman |
| 8,220,690 B2 | 7/2012 | Hess et al. |
| 8,286,845 B2 | 10/2012 | Perry et al. |
| 8,286,846 B2 | 10/2012 | Smith et al. |
| 8,292,153 B2 | 10/2012 | Jankowski |
| 8,303,622 B2 | 11/2012 | Alkhatib |
| 8,317,074 B2 | 11/2012 | Ortiz et al. |
| 8,348,131 B2 | 1/2013 | Omaits et al. |
| 8,365,976 B2 | 2/2013 | Hess et al. |
| 8,424,741 B2 | 4/2013 | McGuckin, Jr. et al. |
| 8,453,913 B2 * | 6/2013 | Milliman ............ A61B 17/115 227/179.1 |
| 8,464,924 B2 | 6/2013 | Gresham et al. |
| 8,485,412 B2 | 7/2013 | Shelton et al. |
| 2003/0014064 A1 | 1/2003 | Blatter |
| 2003/0111507 A1 | 6/2003 | Nunez |
| 2005/0051597 A1 | 3/2005 | Toledano |
| 2005/0059997 A1 | 3/2005 | Bauman et al. |
| 2005/0107813 A1 | 5/2005 | Garcia |
| 2005/0145675 A1 | 7/2005 | Hartwick et al. |
| 2005/0187616 A1 | 8/2005 | Realyvasquez |
| 2005/0202640 A1 | 9/2005 | Fitzgerald et al. |
| 2005/0205640 A1 * | 9/2005 | Milliman ............ A61B 17/115 227/176.1 |
| 2005/0209685 A1 | 9/2005 | Shifrin et al. |
| 2005/0263561 A1 | 12/2005 | Sharma et al. |
| 2006/0000869 A1 | 1/2006 | Fontayne |
| 2006/0011698 A1 | 1/2006 | Okada et al. |
| 2006/0049234 A1 | 3/2006 | Flak et al. |
| 2006/0124688 A1 * | 6/2006 | Racenet ............ A61B 17/0644 227/175.1 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0088389 A1 | 4/2007 | Dunkin et al. |
| 2008/0078802 A1 | 4/2008 | Hess et al. |
| 2008/0140115 A1 | 6/2008 | Stopek |
| 2008/0185419 A1 | 8/2008 | Smith et al. |
| 2008/0190989 A1 | 8/2008 | Crews et al. |
| 2008/0190991 A1 | 8/2008 | Milliman |
| 2008/0251569 A1 | 10/2008 | Smith et al. |
| 2009/0206142 A1 * | 8/2009 | Huitema ......... A61B 17/07207 227/176.1 |

FOREIGN PATENT DOCUMENTS

| | | |
|---|---|---|
| EP | 1949861 | 7/2008 |
| EP | 2090233 | 8/2009 |
| JP | 10-156942 | 6/1998 |
| WO | WO02/32322 | 4/2002 |
| WO | WO03/094745 | 11/2003 |
| WO | WO2005/009216 | 2/2005 |
| WO | WO2008/039237 | 4/2008 |

OTHER PUBLICATIONS

Japanese Office Action dated Mar. 13, 2014.
European Search Report 10250199 dated Jul. 3, 2012.
Australian Office Action dated Feb. 22, 2016, issued in Australian Application No. 2015202213.

* cited by examiner

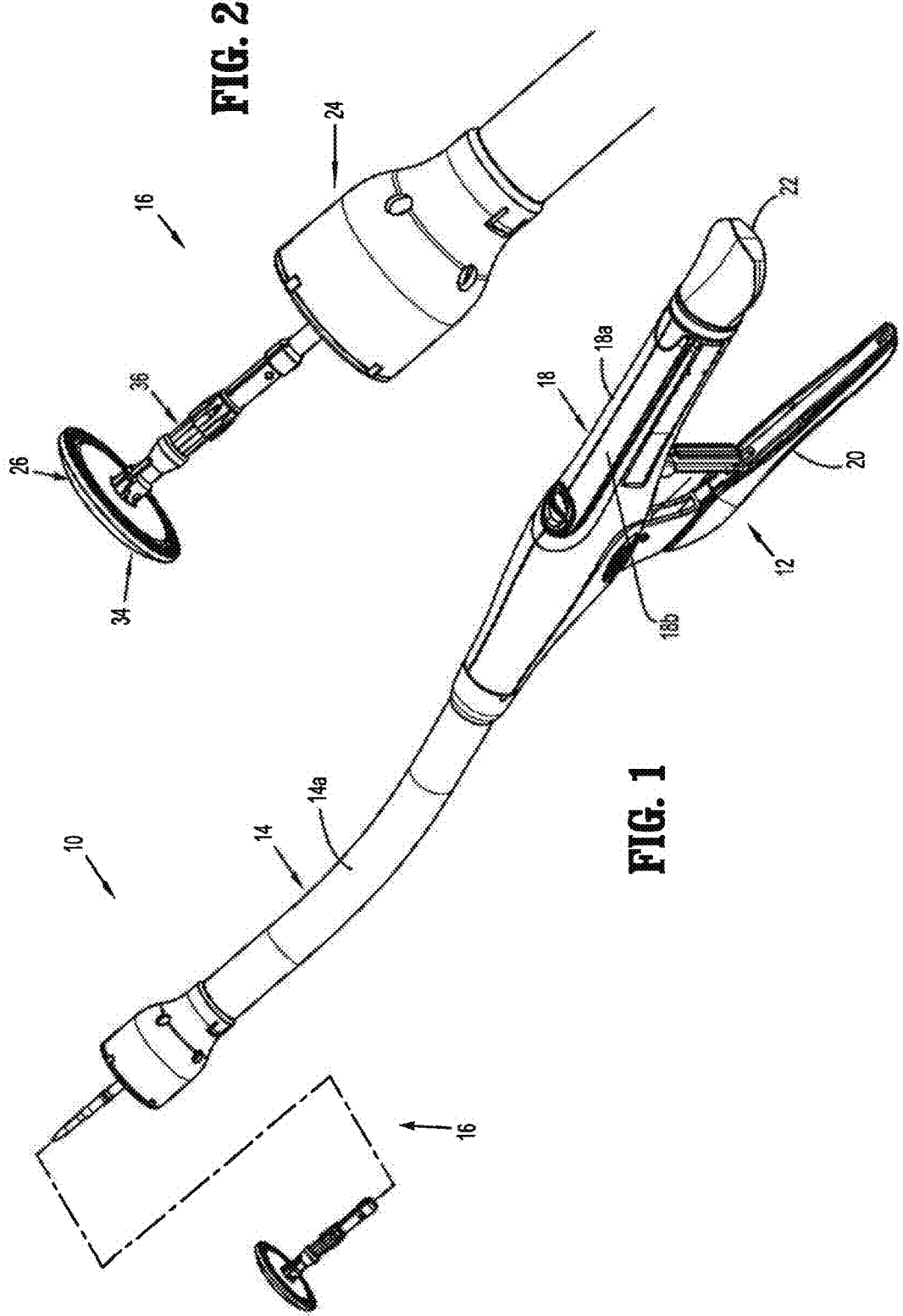

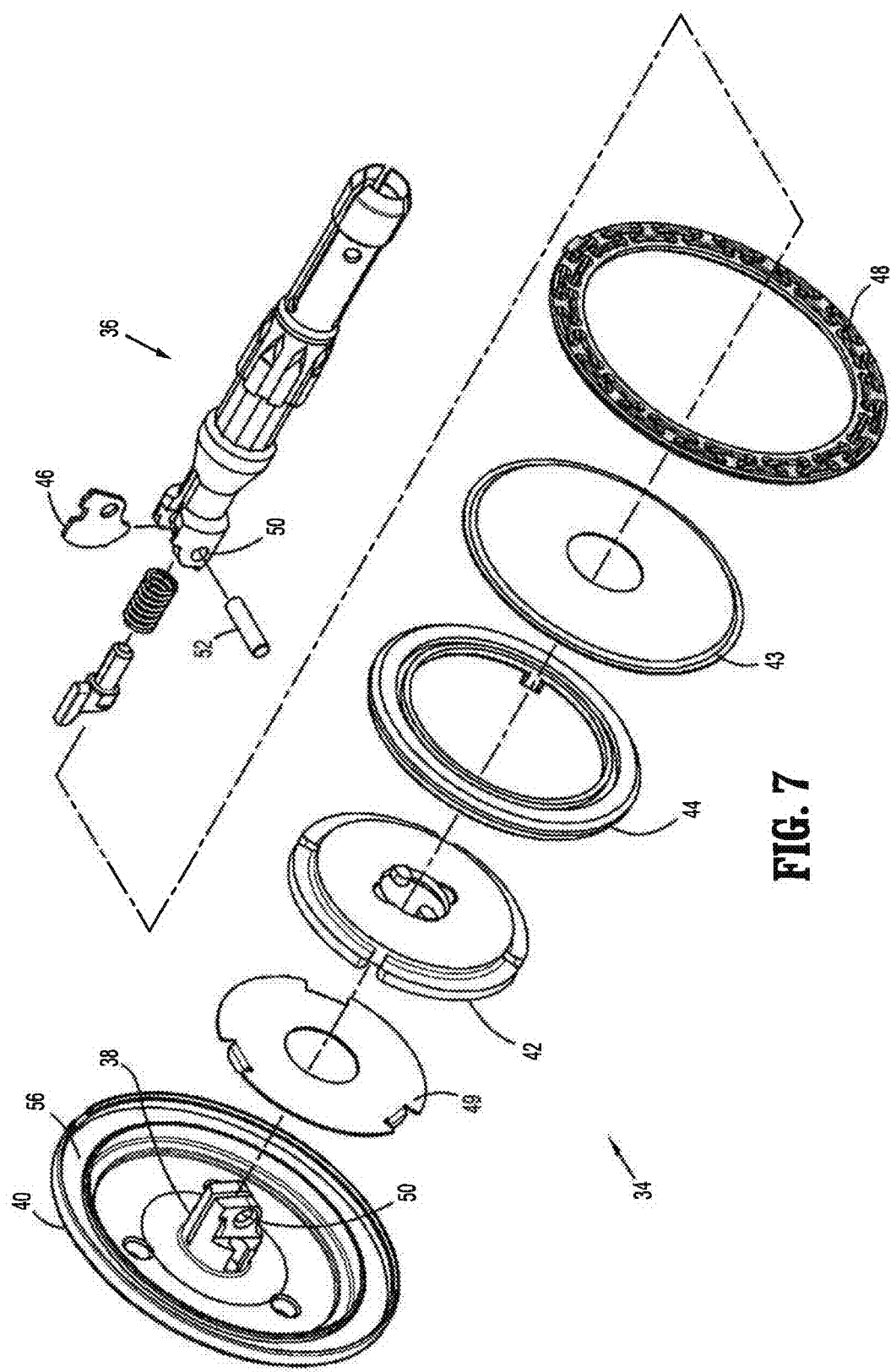

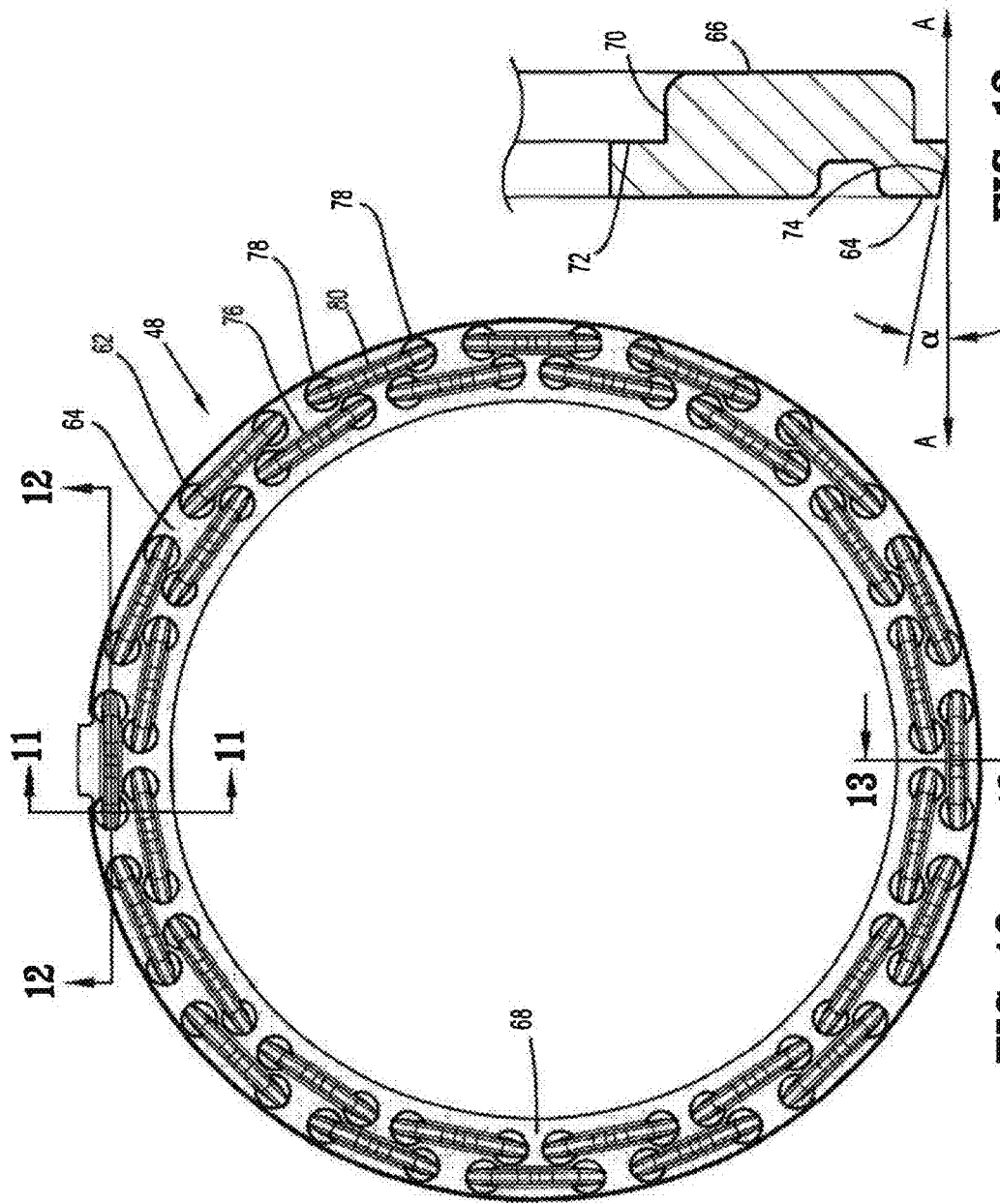
FIG. 13
FIG. 10
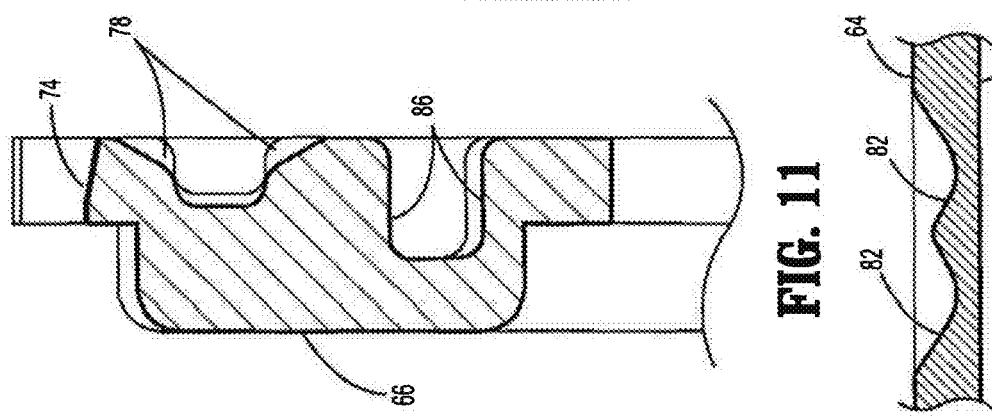
FIG. 11
FIG. 12

ANVIL FOR SURGICAL STAPLER

CROSS-REFERENCE TO RELATED APPLICATIONS

This application is a divisional of U.S. patent application Ser. No. 12/688,870, filed on Jan. 16, 2010, now U.S. Pat. No. 8,453,913, which claims the benefit of, and priority to, U.S. Provisional Patent Application Ser. No. 61/150,429, filed on Feb. 6, 2009, now expired, the entire content of each of the applications identified above being incorporated by reference herein.

BACKGROUND

1. Technical Field

The present disclosure relates to surgical fastener applying apparatus, and more particularly, to an anvil assembly for use therewith, as well as methods of manufacturing the same.

2. Background of the Related Art

Many varieties of surgical fastener applying apparatus are known in the art, some of which are specifically adapted for use in various surgical procedures such as end-to-end anastomosis, circular end-to-end anastomosis, open gastrointestinal anastomosis, endoscopic gastrointestinal anastomosis, and transverse anastomosis. Suitable examples of fastener applying apparatus that may be used during the course of such procedures can be seen in U.S. Pat. Nos. 5,915,616; 6,202,914; 5,865,361; and 5,964,394.

Surgical fastener applying apparatus for use in performing circular anastomosis of hollow tissue organs generally include an anvil assembly incorporating an anvil head and an anvil plate. The anvil plate includes pockets that are configured and dimensioned to receive and form the surgical fasteners to join together adjacent sections of the patient's tissue. The fastener pockets are typically arranged into one or more rows positioned on opposite sides of, or about, a cutting element or a corresponding channel adapted for the receipt of the cutting element.

In these apparatus, the anvil head and the anvil plate are often assembled through welding, by forming retention tabs over the anvil plate and staking the anvil head and the anvil plate together, or by swaging a rib over the anvil plate. However, when the anvil head and the anvil plate are formed from different materials, welding may be inapplicable, while staking and swaging of the aforementioned rib may result in the formation of a protrusion that may in certain instances affect tissue clamped between the anvil head and the anvil plate.

When surgical fasteners are applied to tissue, proper formation is desirable for many different reasons, including the minimization of bleeding and the effectuation of hemostasis. In order to ensure accurate and consistent formation of surgical fasteners, considerable research and development has been conducted in the areas of forming and driving structures, and strict manufacturing tolerances have been implemented. For example, anvil assemblies such as those described in U.S. Pat. Nos. 5,173,133 and 5,480,089 have been developed with specific coatings and/or structure, and fastener cartridges such as those described in commonly assigned U.S. Pat. No. 4,978,049 include driver structure that is configured and dimensioned to balance forces encountered during staple formation.

Consequently, it would be advantageous to provide an anvil assembly for use with a surgical fastener applying apparatus that includes an anvil head and an anvil plate formed from different materials and incorporating design features that will address these issues of manufacture and fastener formation.

SUMMARY

In one aspect of the present disclosure, an anvil assembly is disclosed for use with a surgical fastener applying apparatus. The anvil assembly includes an anvil head defining a longitudinal axis and formed from a first material and an anvil plate that is supported by the anvil head. The anvil plate includes a plurality of fastener pockets, and is formed from a second material different from the first material. In one embodiment of the anvil assembly, the second material may be selected from the group consisting of steel, titanium, magnesium, aluminum, and zinc alloy.

The anvil plate includes a tissue contacting surface, and may be of die-cast construction. In one embodiment, the tissue contacting surface of the anvil plate may include a coating formed from a third material that is different from each of the first and second materials, such as a nickel Teflon coating for example.

The anvil plate preferably includes an anvil body and an outer step extending radially outward from the anvil body. The anvil plate preferably further includes an outer side wall that tapers towards the longitudinal axis of the anvil head to form an acute angle with the longitudinal axis of the anvil head. In one embodiment of the anvil plate, the acute angle defined between the outer side wall and the longitudinal axis lies substantially within the range of approximately 5 degrees to approximately 15 degrees, and in another embodiment, the acute angle can be approximately equal to 11 degrees.

The anvil head preferably includes an annular recess that is configured and dimensioned to receive the anvil plate. The anvil head preferably further includes an annular shoulder positioned about the annular recess that is configured and dimensioned to support the outer step of the anvil plate, as well as an annular lip formed at the distal end thereof.

The anvil plate is preferably secured within the annular recess by deforming the annular lip radially inward into contact with the tapered side wall of the anvil plate. After deformation, at least a portion of the annular lip thus preferably forms the same acute angle with the longitudinal axis defined between the outer side wall of the anvil plate and the longitudinal axis and so that the lip is preferably substantially flush with the anvil plate.

The anvil assembly may further comprise a center rod that is pivotally connected to the anvil head such that the anvil head is movable through a predetermined sector of rotation which could be substantially within the range of approximately 0 degrees to approximately 270 degrees.

In another aspect of the present disclosure, a method of manufacturing an anvil assembly for use with a surgical fastener applying apparatus is disclosed. The method includes the steps of providing an anvil head defining a longitudinal axis, providing an anvil plate, positioning the anvil head and the anvil plate in contacting relation, and deforming a portion of the anvil head towards the anvil plate to fixedly secure the anvil head and the anvil plate together such that the anvil assembly includes a substantially uniform proximal-most surface. The anvil plate preferably includes an outer side wall that tapers radially towards the longitudinal axis of the anvil head such that an acute angle is defined between the outer side wall and the longitudinal axis.

In the disclosed method, the anvil head and the anvil plate are preferably formed from different materials, i.e., the anvil head is formed from a first material and the anvil plate is formed from a second, different material. In one embodiment, the second material comprising the anvil plate may be selected from the group consisting of steel, titanium, magnesium, aluminum, and zinc alloy.

In another aspect of the present disclosure, a surgical fastener applying apparatus is disclosed that includes a surgical fastener retention assembly accommodating a plurality of surgical fasteners each having first and second legs, and an anvil assembly including a tissue contacting surface with a plurality of fastener pockets formed therein. Each fastener pocket includes a pair of cavities that are each configured and dimensioned to receive a corresponding leg of one of the surgical fasteners. The cavities are connected by a linear section including a pair of arcuate forming surfaces that are each configured and dimensioned to engage and redirect a corresponding leg of the surgical fastener to achieve a formed configuration. The cavities may be substantially spherical in configuration, which provide increased surface area for contact with the legs of the surgical fastener and assist in guiding the legs of the surgical fasteners into contact with the arcuate forming surface.

Each cavity preferably defines an outer rim at least partially intersecting one of the forming surfaces.

In one embodiment of the surgical fastener applying apparatus, each fastener pocket includes a pair of substantially planar side walls that extend from at least a portion of the forming surfaces towards the tissue contacting surface.

It is envisioned that the anvil assembly may include an anvil head and an anvil plate, wherein the fastener pockets are formed in the anvil plate. It is further envisioned that anvil head may be formed from a first material, while the anvil plate may be formed from a second, different material, and the tissue contacting surface of the anvil plate may have a coating formed from a third material. The anvil plate may include an outer side wall that tapers towards the longitudinal axis of the anvil head such that an acute angle is defined between the outer side wall and the longitudinal axis.

These and other features of the surgical fastener applying apparatus, and the anvil assembly for use therewith, disclosed herein will become more readily apparent to those skilled in the art through reference to the following detailed description of various embodiments of the present disclosure.

BRIEF DESCRIPTION OF THE DRAWINGS

Various embodiments of the presently disclosed surgical fastener applying apparatus and anvil assembly for use therewith will be described herein with references to the accompanying drawings, wherein:

FIG. 1 is a top, perspective view of a surgical fastener applying apparatus including a distal head portion in accordance with the principles of the present disclosure;

FIG. 2 is a side, perspective view of the distal head portion seen in FIG. 1 illustrating a surgical fastener retention assembly and an anvil assembly;

FIG. 7 is a side, perspective view of the anvil assembly of FIG. 2 with parts separated;

FIG. 10 is a top view of the anvil plate;

FIG. 11 is a cross-sectional view of the anvil plate taken through line 11-11 in FIG. 10;

FIG. 12 is a cross-sectional view of the anvil plate taken through line 12-12 in FIG. 10;

FIG. 13 is a cross-sectional view of the anvil plate taken through line 13-13 in FIG. 10;

DETAILED DESCRIPTION OF EXEMPLARY EMBODIMENTS

Figure 3A:
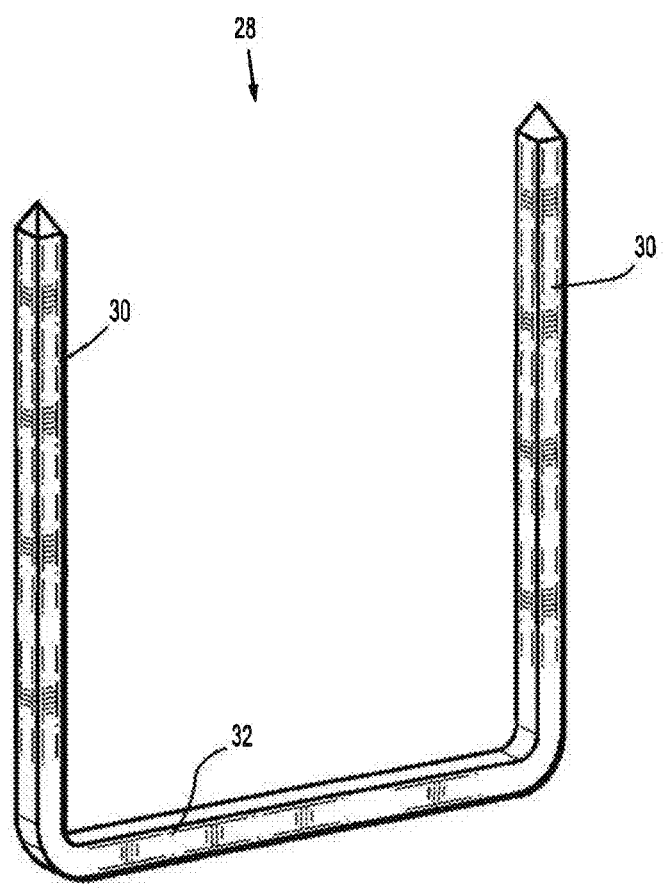
FIG. 3A is a front, perspective view of one example of a surgical fastener that may be loaded into the surgical fastener retention assembly seen in FIG. 2.

Various exemplary embodiments of the presently disclosed surgical fastener applying apparatus and anvil assembly for use therewith, as well as methods of manufacturing the same, will now be described in detail with reference to the drawings wherein like references numerals identify similar or identical elements. In the drawings and the following description, the term "proximal" will refer to the end of the surgical fastener applying apparatus, or component thereof, that is closer to the operator during proper use, while the term "distal" will refer to the end of the fastener cartridge that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like.

FIG. 1 illustrates a surgical fastener applying apparatus, referred to generally by reference numeral 10, in accordance with one embodiment of the present disclosure. Briefly, the surgical fastener applying apparatus 10 includes a handle assembly 12, an elongated central body portion 14 with a curved elongated outer tube 14a, and a distal head portion 16. In alternative embodiments of the surgical fastener applying apparatus 10, the length and/or configuration of the central body portion 14 may be altered or varied to suit the requirements of the particular surgical procedure in which the surgical fastener applying apparatus may be employed. For example, when used in a procedure for the treatment of hemorrhoids, the central body portion 14 may be substantially straight, as opposed to curved, and may be shortened. The transverse dimensions of the body portion 14 and/or the head portion 16 may also be varied to suit a particular surgical procedure.

The handle assembly 12 includes a stationary handle 18, a firing trigger 20, and a rotatable approximation knob 22. In the embodiment of the surgical fastener applying apparatus 10 shown in FIG. 1, the stationary handle 18 includes a pair of thermoplastic handle sections 18a, 18b, e.g., polycarbonate, which together define a housing for the internal components of the handle assembly 12. The handle sections 18a, 18b can be secured together by sonic welding, or any other known securement technique, such as through the use of screws, adhesives, snap-fit connectors, etc.

As seen in FIG. 2, the head portion 16 includes a surgical fastener retention assembly 24 and an anvil assembly 26. The surgical fastener retention or shell assembly 24 accommodates a plurality of surgical fasteners 28, an example of which can be seen in FIG. 3A, used to attach adjacent portions of a patient's tissue. As seen in FIG. 3A, each surgical fastener 28 includes a pair of legs 30 connected by a backspan 32. The surgical fastener retention assembly 24 also performs additional functions and includes additional components, each of which is discussed in commonly assigned U.S. Pat. No. 7,556,186, the entire contents of which are incorporated by reference herein.

Referring now to FIGS. 4-16, the anvil assembly 26 extends along a longitudinal axis "A-A," and includes an anvil head assembly 34 and an anvil center rod assembly or anvil shaft 36. The anvil head assembly 34 includes a post 38, an anvil head 40, a backup plate 42, a cutting ring 44, a cutting ring cover 43, a retainer member 49, a cam latch 46 (FIG. 7), and an anvil plate 48. In the embodiment of the anvil head assembly 34 shown in FIGS. 4-15, the post 38 includes a transverse throughbore 50 ((FIG. 7) that is configured and dimensioned to receive a pin 52 such that the anvil head assembly 34 can pivot relative to the center rod assembly 36 through a predetermined sector of rotation 54 (FIG. 6) up to and including about 180 degrees. Rotation through other sectors is also contemplated. It is also envisioned, however, that the anvil head assembly 34 and the center rod assembly 36 may be connected such that there is no pivotal movement.

The present disclosure is directed primarily to the specific structure of the anvil head 40 and the anvil plate 48. Accordingly, only these components of the anvil assembly 26 will be discussed in further detail herein below. However, the features and elements of the remaining components of the anvil head assembly 34, i.e., the post 38, the backup plate 42, the cutting ring 44, and the cam 46, as well as those of the surgical fastener retention assembly 24, are discussed in the aforementioned U.S. Pat. No. 7,556,186.

Figure 5:
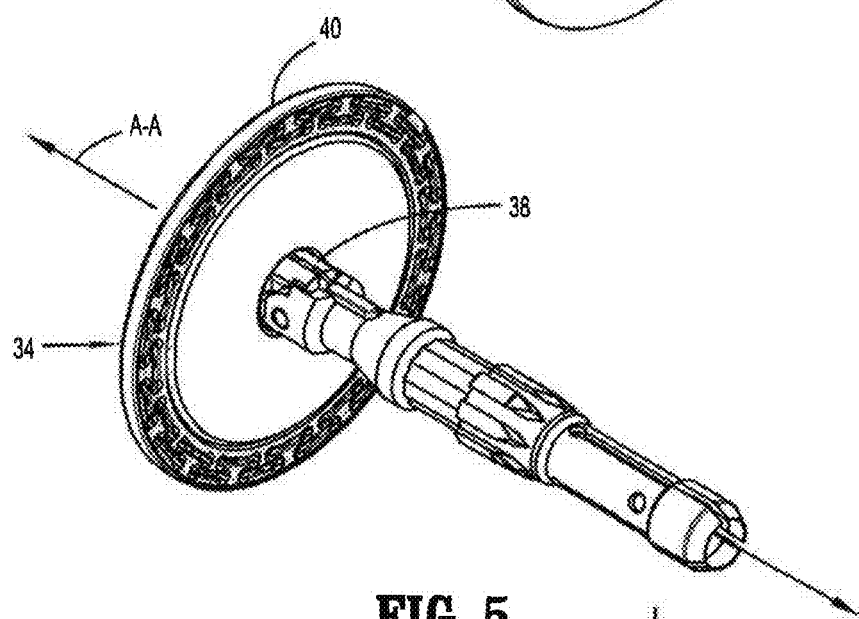
Figure 6:
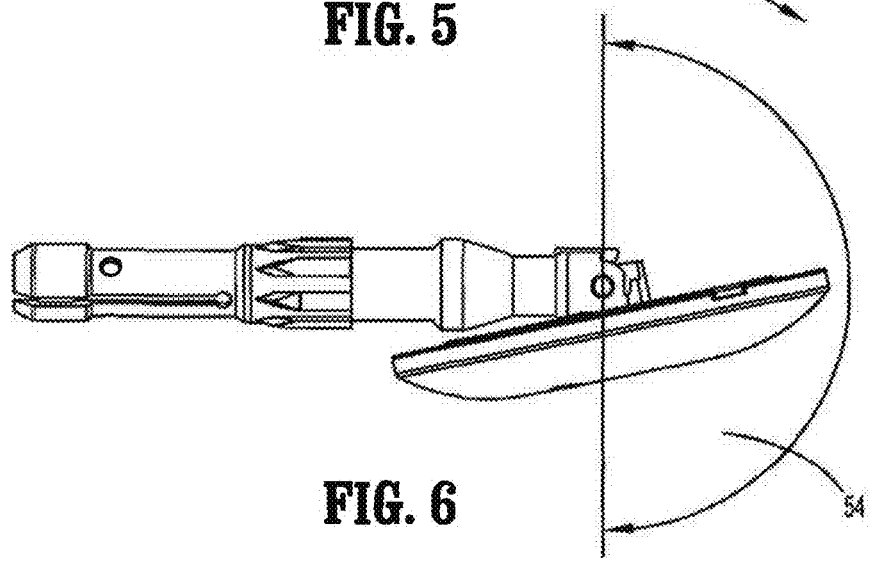
FIG. 6 is a side view of the anvil assembly of FIG. 2 shown in an inoperative tilted position.
Figure 16A:
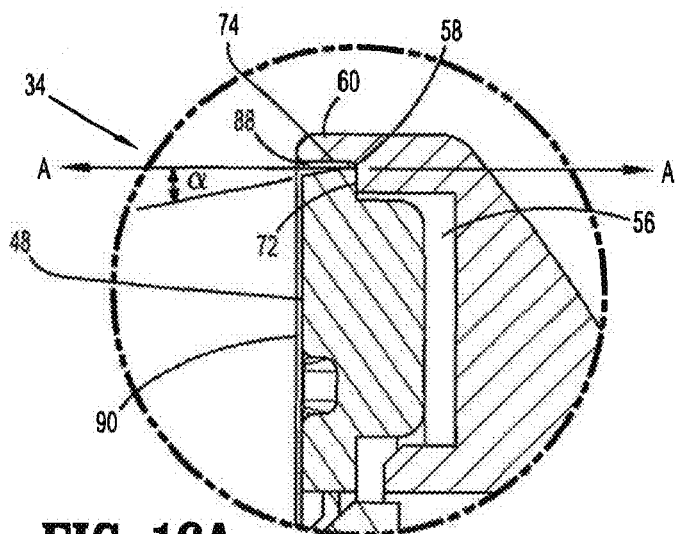
FIGS. 16A and 16B are cross-sectional, enlarged views of the portion of the anvil assembly identified in FIG. 15 before and after deformation of the anvil head in manufacture, respectively.
Figure 16B:
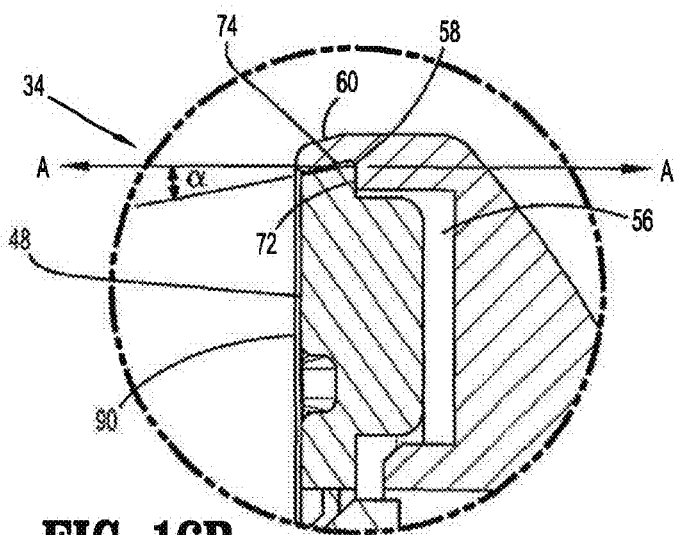

With continued reference to FIGS. 4-16, the anvil head 40 may be formed from any suitable biocompatible material, including but not limited to stainless steel. The anvil head 40 includes an annular recess 56 (FIG. 7) that is configured and dimensioned to receive the anvil plate 48, an annular shoulder 58 (FIGS. 16A, 16B) and an annular lip 60. The annular shoulder 58 is positioned about the annular recess 56, and is configured and dimensioned to support the anvil plate 48. The annular lip 60 is positioned about the annular shoulder 58 and is moved, e.g. deformed, from a first position (FIG. 16A) to a second position (FIG. 16B) during assemblage of the anvil head assembly 34, i.e., following placement of the anvil plate 48 within the annular recess 56 of the anvil head 40. Movement, e.g. deformation, of the annular lip 60 into the second position (FIG. 16B) during manufacture secures the anvil plate 48 within the annular recess 56, and prevents relative movement between the anvil head 40 and the anvil plate 48, e.g., along the longitudinal axis "A-A" (FIG. 5). In this position, the anvil plate 48 is substantially flush with the lip 60 of the anvil head 40 as shown in FIG. 16B.

The anvil plate 48 is preferably a die-cast member that can be formed from any suitable material. Examples of materials suitable for the construction of the anvil plate 48 and the anvil head 40 include, but are not limited to steel, titanium, magnesium, aluminum, or zinc alloy. It is envisioned that the anvil plate 48 and the anvil head 40 may be comprised of the same material, or alternatively, and preferably, the materials comprising the anvil plate 48 and the anvil head 40 may be different. In one embodiment of the anvil assembly 26, the anvil plate 48 is formed from the zinc Zamak #3 alloy, which includes at least 95% zinc, aluminum, magnesium, and copper and the anvil head is formed of stainless steel.

The anvil plate 48 includes a body 62 (FIG. 10) with a tissue contacting surface 64 (FIG. 13) facing proximally and a bottom surface 66 facing distally. In one embodiment of the anvil plate 48, the tissue contacting surface 64 may include a coating 68 (FIGS. 9, 10) formed from a suitable biocompatible material. Including such a coating 68 may reduce the likelihood that the patient's tissue will stick or adhere to the anvil plate 48, and/or enable the anvil plate 48 to be formed from materials that could not otherwise be included in the construction thereof due to bio-incompatibility, e.g., the aforementioned zinc (Zamak #3) alloy. In one particular embodiment of the anvil plate 48, the coating 68 includes a nickel Teflon coating, although the use of other materials is within the scope of the present disclosure.

As seen in FIG. 13, the configuration of the body 62 of anvil plate defines an inner step 70, an outer step 72, and an outer sidewall 74 that extends between the outer step 72 and the tissue contacting surface 64. The outer side wall 74 is tapered towards the longitudinal axis A-A (in a proximal direction toward surface 64)) to define an acute angle .alpha. therewith. In the specific embodiment of the anvil plate 48 seen in FIG. 13, the outer side wall 74 and the longitudinal axis A-A subtend an angle .alpha. that is approximately equal to about 11 degrees. However, in alternative embodiments of the anvil plate 48, the angle .alpha. may be any angle within the range of approximately 0 degrees and approximately 90 degrees.

Referring now to FIGS. 9-12 in particular, the tissue contacting surface 64 of the anvil plate 48 includes a plurality of pockets 76 that are arranged into a plurality of annular rows. As shown, the anvil plate 48 includes two (2) annular rows of pockets 76. It should be appreciated, however, that the rows of pockets 76 may be present in either greater or fewer numbers in alternative embodiments of the anvil plate 48. The pockets 76 include a pair of cavities 78 that are connected by a linear section 80 including a pair of forming surfaces 82.

Figure 9:
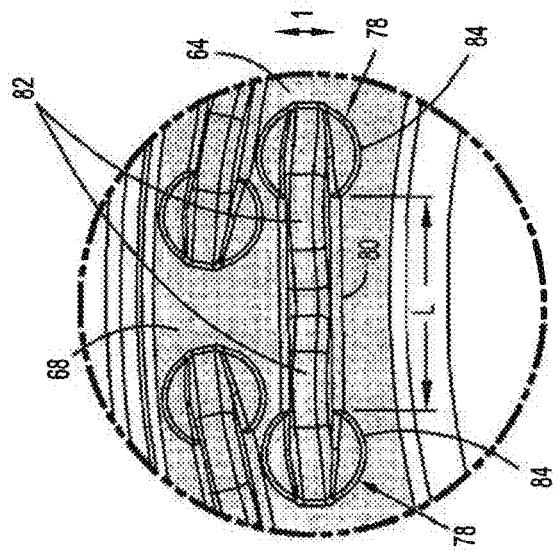
FIG. 9 is an enlarged view of the indicated area of detail shown in FIG. 8.
Figure 8:
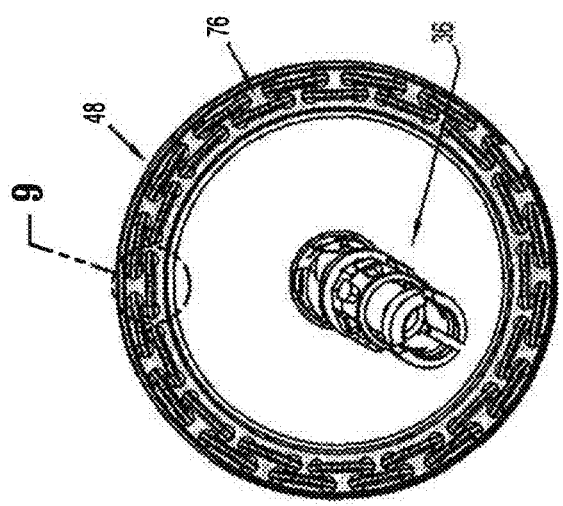
FIG. 8 is an end, perspective view of the anvil assembly seen in FIG. 2.
Figure 14:
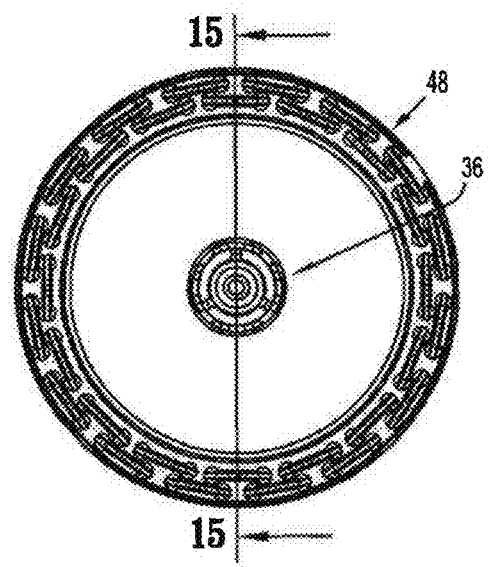
FIG. 14 is an end view of the anvil assembly seen in FIG. 2.
Figure 15:
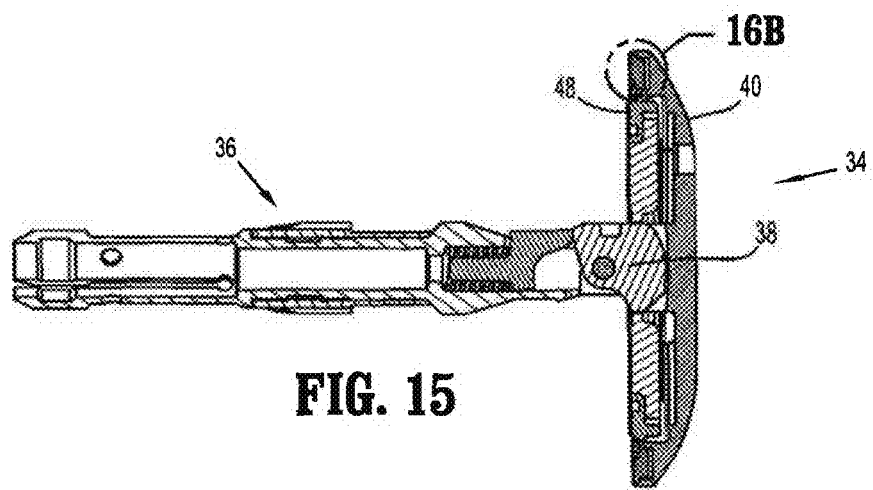
FIG. 15 is a cross-sectional view of the anvil assembly taken through line 15-15 in FIG. 14.

The cavities 78 define an outer rim 84 (FIG. 9), and slope inwardly therefrom, i.e., away from the tissue contacting surface 64. The cavities 78 are configured and dimensioned to urge the legs 30 of the fastener 28 (FIG. 3A) into the linear section 80, and more specifically, into contact with the forming surfaces 82 (FIGS. 9, 12). The presence of the cavities 78, which as shown are substantially circular, relaxes the tolerances of the surgical fastener applying apparatus 10 (FIG. 1) by reducing the precision with which the surgical fasteners must be ejected from the surgical fastener retention assembly 24 (FIG. 2) in order to facilitate contact between the legs 30 (FIG. 3A) of the fasteners 28 and the forming surfaces 82 (FIGS. 9, 12). By reducing such tolerances, the likelihood that an ejected fastener 28 will fail to contact the forming surfaces 82 is reduced. Reducing such tolerances also decreases the costs associated with manufacture of the surgical fastener applying apparatus 10.

In one embodiment of the anvil plate 48, the cavities 78 may be substantially spherical in configuration, as seen in FIG. 9. This configuration increases the surface area of the cavities 78 available for contact with the legs 30 (FIG. 3A) of the fastener 28 when compared to alternate possible configurations for the cavities 78, thus maximizing the likelihood that an ejected fastener 28 will be received and properly formed.

As mentioned above, the cavities 78 are connected by the linear section 80 (FIG. 9). Specifically, at least a portion of the outer rim 84 of each cavity 78 intersects the linear section 80, e.g., to substantially limit any interruption in the movement of the legs 30 of the surgical fastener 28 from the cavities 78 into contact with the forming surfaces 82. The linear section 80 defines a length "L" that is determined based upon the specific dimensions of the fasteners 28 to be formed. Accordingly, the length "L" of the linear section 80 can be varied in alternative embodiments of the anvil plate 48 dependent upon the particular configuration and dimensions of the fasteners 28 (FIG. 3A) loaded into the fastener retention assembly 24 (FIG. 2).

Figure 3B:
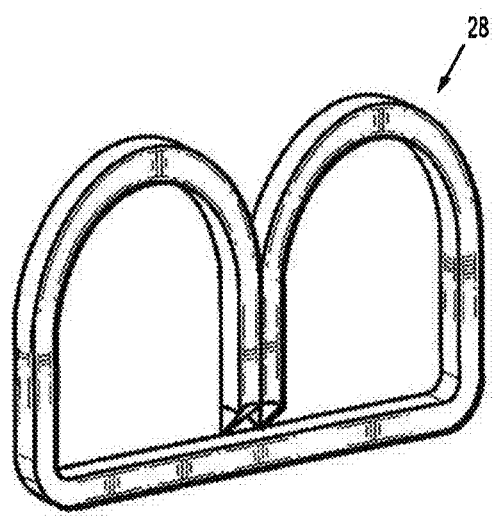
FIG. 3B is a front, perspective view of the surgical fastener shown in FIG. 3A subsequent to formation and including a B-shaped configuration.
Figure 3C:
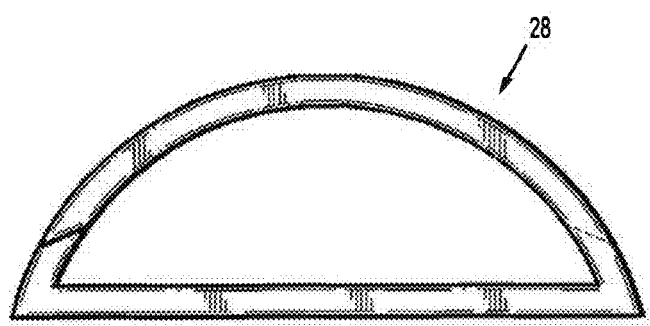
FIG. 3C is a front, schematic view of the surgical fastener shown in FIG. 3A subsequent to formation and including an alternate single-loop configuration.
Figure 4:
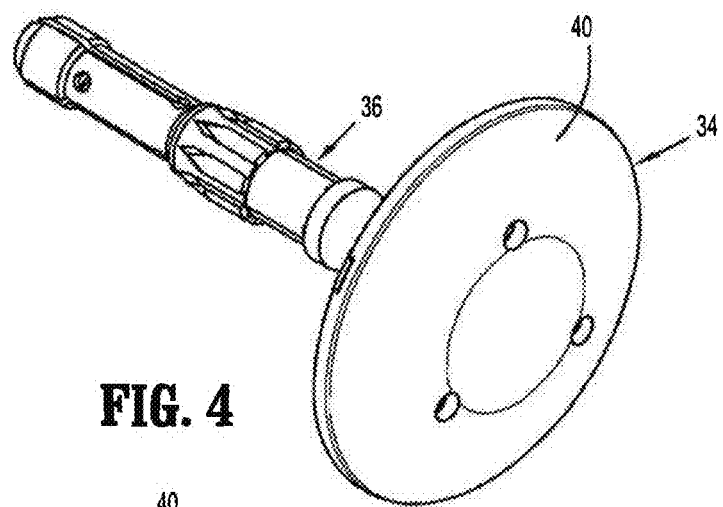
FIGS. 4 and 5 are side, perspective views from opposing ends of the anvil assembly of FIG. 2.

With continued reference to FIGS. 9-12, the forming surfaces 82 are arcuate in configuration along the length "L" of the linear section 80, initially curving away from, and then towards, the tissue contacting surface 64. This curvature promotes redirection and deformation of the legs 30 (FIG. 3A) of the fasteners 28 such that the fasteners 28 can achieve a desired formed configuration. In the embodiment of the anvil plate 48 seen in FIGS. 4-16, the forming surfaces 82 are positioned, configured, and dimensioned such that the fasteners 28 achieve the "B-shaped" configuration seen in FIG. 3B upon formation. In alternative embodiments of the anvil plate 48, however, the position, configuration, and/or dimensions of the forming surfaces 82 can be adjusted to alter the formed configuration of the fasteners 28. For example, the forming surfaces 82 may be positioned, configured, and dimensioned such that the fasteners 28 achieve the single loop configuration seen in FIG. 3C upon formation.

The pockets 76 further include a pair of side walls 86 (FIG. 11) that extend from the forming surfaces 82 to the tissue contacting surface 64. The side walls 86 are configured and dimensioned to further ensure proper formation of the surgical fasteners 28 (FIG. 3A). Specifically, in one embodiment, the side walls 86 define a substantially planar configuration that limits lateral movement of the legs 30 within the fastener pockets 76, i.e., in the direction indicated by arrows 1 (FIG. 9). Restricting such movement maintains contact between the legs 30 of the fasteners 28 (FIG. 3A) and the forming surfaces 82 until formation of the fasteners 28 is complete, thus increasing the likelihood of proper formation of the surgical fasteners 28. Although shown as substantially perpendicular to the forming surfaces 82, alternatively, the side walls 86 can extend at an acute angle to the forming surface so long as they achieve the lateral movement restriction function.

The manufacture and assemblage of the anvil assembly 34 will now be discussed. After casting, the anvil plate 48 can be positioned within the annular recess 56 formed within the anvil head 40 such that the outer step 72 (FIG. 16A) of the anvil plate 48 is positioned in contact with the annular shoulder 58 of the anvil head 40. When so positioned, the outer side wall 74 forms the aforementioned angle .alpha. with the longitudinal axis A-A, and defines a gap 88 (FIG. 16A) with the annular lip 60 of the anvil head 40. Thereafter, the annular lip 60 is deformed radially inward, i.e., towards the longitudinal axis A-A, until the annular lip 60 contacts the outer side wall 74 (FIG. 16B). After deformation, at least a portion of the annular lip 60 forms the same acute angle .alpha. with the longitudinal axis A-A defined between the outer side wall 74 of the anvil plate 48 and the longitudinal axis A-A. The annular lip 60 may be deformed through any suitable method, including but not limited to swaging. The taper of the outer side wall 74, and the gap 88 created with the annular lip 60 of the anvil head 40, allow the annular lip 60 to be positioned substantially flush with the forming surfaces 82 of the anvil plate 48 to thereby define a proximal-most surface 90 (FIG. 16B) that is substantially uniform and substantially planar in configuration. Were the bevel of the outer side wall 74, and the corresponding gap 88, to be omitted, deforming the annular lip 60 radially inward as described may result in the formation of a projection, protuberance, or other irregularity on the proximal-most surface of the anvil assembly 34, i.e., the surface of the anvil assembly 34 that comes into contact with the patient's tissue. The flush proximal-most surface 90 realized upon assemblage of the anvil head 40 and the anvil plate 48 avoid such formations.

Figure 17:
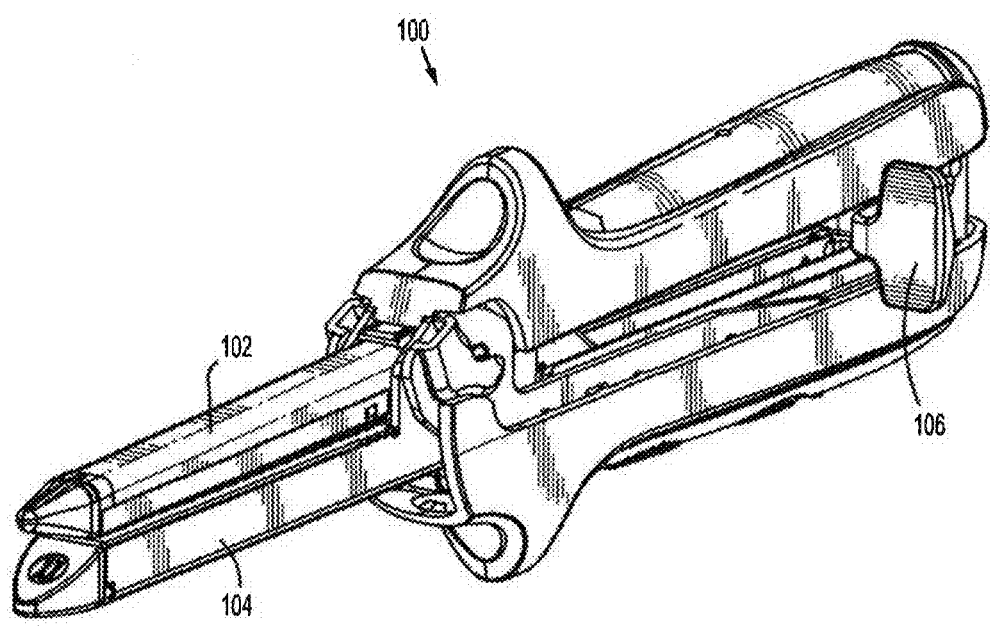
FIG. 17 illustrates an open anastomosis surgical fastener applying instrument in accordance with one embodiment of the present disclosure.
Figure 18:
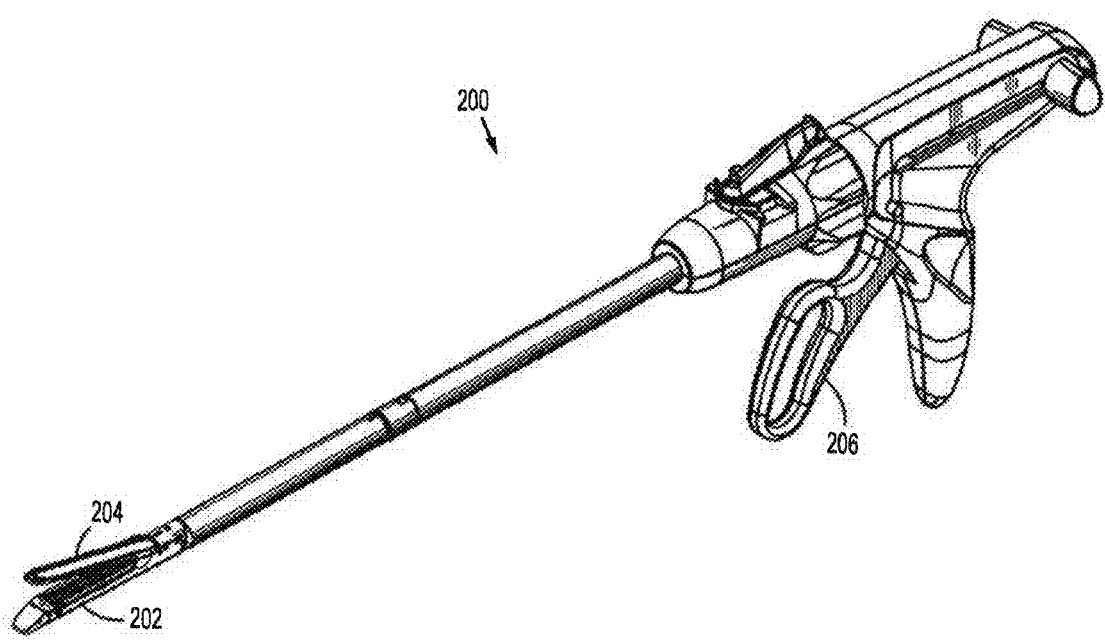
FIG. 18 illustrates an endoscopic anastomosis surgical fastener applying instrument in accordance with another embodiment of the present disclosure.
Figure 19:
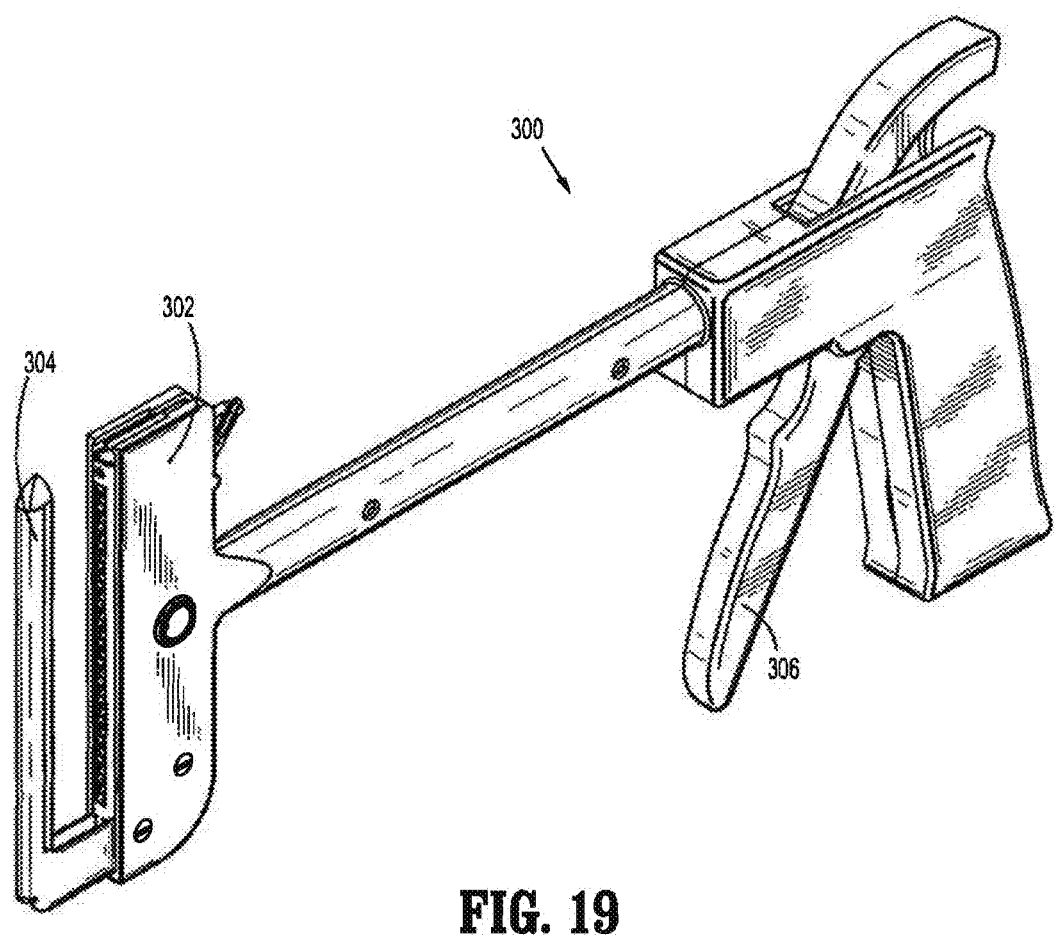
FIG. 19 illustrates a transverse anastomosis fastener applying instrument in accordance with still another embodiment of the present disclosure.

While the coating 68 (FIG. 10) and the fastener pockets 76 have been discussed and illustrated in connection with the surgical fastener applying apparatus 10, which is suitable for use in an end-to-end anastomosis surgical procedure, it should be appreciated that the coating 68 and the novel geometry of the fastener pockets 76 may be employed in any surgical fastener applying apparatus. For example, the fastener pockets 76 may be incorporated into an open gastrointestinal anastomosis apparatus 100 (FIG. 17), an endoscopic gastrointestinal anastomosis 200 (FIG. 18), or a transverse anastomosis apparatus 300 (FIG. 19). The apparatus 100 has a pair of jaws 102, 104 for clamping tissue and a knob 106 movable distally to apply linear rows of surgical fasteners transverse to the longitudinal axis of the apparatus 100. Apparatus 200 has a movable staple jaw 202 and an anvil jaw 204 for clamping tissue. Actuation of handle 206 fires the fasteners in a direction transverse to the longitudinal axis of the apparatus 200. Apparatus 300 has a movable cartridge assembly 302 advanceable distally towards anvil 304 to clamp tissue therebetween. Handle 306 fires the fasteners in a direction substantially parallel to a longitudinal axis of the apparatus 300.

The above description, disclosure, and figures should not be construed as limiting, but merely as exemplary of particular embodiments. It is to be understood, therefore, that the disclosure is not limited to the precise embodiments described, and that various other changes and modifications may be effected therein by one skilled in the art without departing from the scope or spirit of the disclosure. Additionally, persons skilled in the art will appreciate that the features illustrated or described in connection with one embodiment may be combined with those of another, and that such modifications and variations are also intended to be included within the scope of the present disclosure.

The invention claimed is:

1. A method of manufacturing an anvil assembly for use with a surgical fastener applying apparatus, the method comprising:

providing an anvil head defining a central longitudinal axis;

providing an anvil plate including an outer side wall that tapers along a linear slope towards the central longitudinal axis of the anvil head;

positioning the anvil head and the anvil plate in contacting relation; and deforming a portion of the anvil head towards the anvil plate to fixedly secure the anvil head and the anvil plate together such that the anvil assembly includes a substantially uniform proximal-most surface.

2. The method of claim 1, wherein providing the anvil head and providing the anvil plate includes providing the anvil head such that the anvil head is formed from a first material, and providing the anvil plate such that the anvil plate is formed from a second material different from the first material.

3. The method of claim 2, wherein providing the anvil head includes providing the anvil head such that the second material is selected from the group consisting of steel, titanium, magnesium, aluminum, and zinc alloy.

4. The method of claim 2, wherein providing the anvil plate includes providing a tissue contacting surface with a coating formed from a third material different from each of the first and second materials.

5. The method of claim 4, wherein providing the anvil plate includes providing the anvil plate such that the third material comprises a nickel nonstick coating.

6. The method of claim 1, wherein deforming the portion of the anvil head includes deforming an annular lip of the anvil head towards the anvil plate such that the annular lip is substantially flush with the anvil plate.

7. The method of claim 1, wherein deforming the portion of the anvil head includes deforming the annular lip such that the annular lip forms an acute angle with the central longitudinal axis.

8. The method of claim 7, wherein deforming the portion of the anvil head includes moving the annular lip towards the anvil plate such that the acute angle lies within the range of approximately 5 degrees to approximately 15 degrees.

9. The method of claim 1, wherein providing the anvil plate includes providing a tissue contacting surface with an annular configuration.

10. The method of claim 1, wherein positioning the anvil head and the anvil plate in contacting relation includes positioning the anvil plate within an annular recess formed in the anvil head.

* * * * *